(12) United States Patent
Duineveld et al.

(10) Patent No.: US 9,040,938 B2
(45) Date of Patent: May 26, 2015

(54) DEVICE COMPRISING A SOURCE FOR EMITTING ULTRAVIOLET LIGHT

(75) Inventors: Paulus Cornelis Duineveld, Drachten (NL); Eva Mondt, Eindhoven (NL); Harko Jan Taekema, Drachten (NL); Willem Sjouke Wijma, Opeinde (NL); Marc Alexander Pastoors, Gieten (NL); Wilhelmus Hendrikus Maria Bruggink, Ureterp (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 336 days.

(21) Appl. No.: 13/389,667

(22) PCT Filed: Aug. 12, 2010

(86) PCT No.: PCT/IB2010/053650
§ 371 (c)(1),
(2), (4) Date: Feb. 9, 2012

(87) PCT Pub. No.: WO2011/018767
PCT Pub. Date: Feb. 17, 2011

(65) Prior Publication Data
US 2012/0138816 A1 Jun. 7, 2012

(30) Foreign Application Priority Data
Aug. 13, 2009 (EP) ..................... 09167768

(51) Int. Cl.
*G01N 21/01* (2006.01)
G01N 21/51 (2006.01)
*G01N 23/10* (2006.01)
(Continued)

(52) U.S. Cl.
CPC . *C02F 1/325* (2013.01); *A61L 2/10* (2013.01); *C02F 2201/3223* (2013.01); *C02F 2201/3228* (2013.01); *C02F 2201/328* (2013.01); *C02F 2301/022* (2013.01)

(58) Field of Classification Search
CPC ....................................... G21K 5/00

USPC ............. 250/437, 436, 434, 432 R, 431, 428, 250/438, 455.11; 202/81, 158; 210/745; 261/94
See application file for complete search history.

(56) References Cited

U.S. PATENT DOCUMENTS 5,302,356 A     4/1994   Shadman et al.
5,888,388 A *   3/1999   Kirk ......................... 210/170.09
(Continued)

FOREIGN PATENT DOCUMENTS

CN     85202067 U   *   7/1986
CN     85202067 U     7/1986
(Continued)

OTHER PUBLICATIONS

R. Iranpour et al; "Hydraulic Effects on Ultraviolet Disinfection: Modification of Reactor Design", Research Jour. of the Water Pollution Control Feferation, Alexandria, VA, Jan. 1, 1000, vol. 71, No. 1 pp. 114-118, XP002223031.

Primary Examiner — David Porta
Assistant Examiner — Meenakshi Sahu

(57) ABSTRACT

A device (1) comprises a source (20) for emitting ultraviolet light, an inlet (30) for letting in fluid to the device (1), an outlet (40) for letting out fluid from the device (1), and means (51, 52) for performing a straightening action of a flow of fluid through the device (1). The flow straightening means comprise at least one flow straightening element (51, 52) having inlet openings for letting in fluid at one side and outlet openings for letting out fluid at another side, wherein each inlet opening is in communication with a plurality of outlet openings, and wherein the element (51, 52) comprises a maze of randomly arranged, interconnected holes. In such a structure, a water element that is moving from one side of the element (51, 52) to another side may take one of various paths, as a result of which variations in inlet conditions can be dampened.

14 Claims, 5 Drawing Sheets

(51) Int. Cl.
  *G01N 23/12* (2006.01)
  *C02F 1/32* (2006.01)
  *A61L 2/10* (2006.01)

(56) References Cited

U.S. PATENT DOCUMENTS

| | | | |
|---|---|---|---|
| 7,511,281 B2 * | 3/2009 | Cooper | 250/432 R |
| 2006/0192136 A1 | 8/2006 | Gadgil et al. | |
| 2007/0290144 A1 * | 12/2007 | Sief et al. | 250/438 |

FOREIGN PATENT DOCUMENTS

| | | | | |
|---|---|---|---|---|
| CN | 1864843 | A | | 11/2006 |
| CN | 1864843 | A | * | 11/2006 |
| CN | 201186173 | Y | | 1/2009 |
| CN | 201186173 | Y | * | 1/2009 |
| EP | 0306301 | A1 | | 3/1989 |
| EP | 0697374 | A1 | | 8/1994 |
| EP | 1837309 | A1 | | 9/2007 |
| JP | 05004091 | A | | 1/1993 |
| JP | 09225458 | A | | 9/1997 |
| JP | 11276558 | A | | 10/1999 |
| JP | 2004025184 | A | | 1/2004 |
| JP | 2005163243 | A | | 6/2005 |
| JP | 2007152155 | A | | 6/2007 |
| JP | 2008093549 | A | | 4/2008 |

* cited by examiner

DEVICE COMPRISING A SOURCE FOR EMITTING ULTRAVIOLET LIGHT

FIELD OF THE INVENTION

The present invention relates to a device, comprising a source for emitting ultraviolet light, an inlet for letting in fluid to the device, an outlet for letting out fluid from the device, and means for performing a straightening action on a flow of fluid through the device, wherein the flow straightening means are arranged in a fluid path from the inlet to the outlet.

BACKGROUND OF THE INVENTION

A well-known example of a device as defined in the preceding paragraph is a device for disinfecting water, in which the element which is arranged inside the housing is a source such as a lamp for emitting ultraviolet light, in particular of the type commonly referred to as UV-C. Exposing infected water to the ultraviolet light has a purifying effect on the water on the basis of the fact that the UV-C light is capable of sterilizing germs. For domestic applications, the ultraviolet source is usually enclosed in a non-opaque holding structure, enabling the desired exposure of the water to the source.

For sufficient germicidal action, the ultraviolet disinfecting device has to produce a certain ultraviolet dose, expressed in $J/m^2$. The dose is given by the irradiance ($W/m^2$) multiplied by a residence time (s) of the bacteria in the device. The residence time as mentioned is determined by the flow paths of the water, and the irradiance level by the type of ultraviolet source which is applied.

The use of flow straightening means in a water disinfecting device is known from EP 1837309, for example. The known flow straightening means comprise a cylinder-shaped element which is provided with a number of perforated sheets, wherein each of the sheets comprises a grid of lamellae and star-shaped openings. The perforated sheets are formed by subjecting a basic sheet to a punching process, and subjecting the perforated sheet which is obtained to a stretching process. The lamellae and the openings are arranged in a regular pattern, and the sheets are arranged in parallel such as to form a stack, in a specific way, namely such that the patterns of the lamellae and the openings of adjacent sheets have a defined shifted arrangement.

When designing a water disinfecting device, it has to be kept in mind that the irradiance of the ultraviolet source decays linearly, or, depending on the extent to which absorption takes place, linearly and exponentially with the radial distance to the source. In view of this fact, in order to achieve a desired effectiveness of the device, it is advantageous if measures are taken to ensure that radial mixing of the water elements takes place. By providing for radial mixing it is intended that all water elements pass the ultraviolet source on a very short distance at some point. Irradiance levels close to the source are so large that a short exposure of the bacteria in the vicinity of the source is sufficient to eliminate them.

It follows from the foregoing that radial mixing is a way of achieving a required dose in a limited exposure time or compact design. However, when radial mixing is applied, several aspects need to be taken into account. In the first place, a mixing element covers the ultraviolet source, at least to a certain extent, and thereby leads to a decrease in irradiance level. Thus, applying a mixing element is only useful when the gain in dose level as a result of an improved flow profile overcomes the losses as a result of a lower irradiance level. Transparent mixing elements can also be used, but such means must be resistant to ultraviolet light and may not be too fragile (glass). It is possible to use upstream static mixing elements which do not have a decreasing effect on the irradiation level, but in that case, the mixing level decays along a length of the device. Consequently, in that case, the highest radial mixing occurs in an inlet area of the device, whereas mixing, and specifically radial mixing, in a downstream area may be minimal or absent. In the second place, it is a fact that water disinfecting devices are mostly used in areas where tap pressure is low. Adding a mixing element may lead to unwanted high pressure drops.

Another problem that is encountered in the field of water disinfecting devices is that so-called short-cuts may be present. Short-cuts are flow paths leading directly from the inlet to the outlet. Bacteria following these short-cuts have very short residence times. Especially when the short-cuts prevail at an outer radius of a section where the ultraviolet source is arranged, remote from the ultraviolet source, at which location irradiance levels are lowest, very low dose levels result. Short-cuts are generally caused by certain inflow conditions and/or inappropriate mixing.

SUMMARY OF THE INVENTION

It is an object of the present invention to provide a solution to the above-sketched problem. In particular, it is an object of the present invention to provide a device comprising an ultraviolet source and means for controlling the flow of fluid through the device, such that there are less short-cuts or even no short-cuts at all, wherein such means are easy to manufacture and not expensive.

According to the present invention, a device is provided, which comprises a source for emitting ultraviolet light, an inlet for letting in fluid to the device, an outlet for letting out fluid from the device, and means for performing a straightening action on a flow of fluid through the device, wherein the flow straightening means are arranged in a fluid path from the inlet to the outlet, and wherein the flow straightening means comprise at least one element having inlet openings for letting in fluid at one side and outlet openings for letting out fluid at another side, wherein each inlet opening is in communication with a plurality of outlet openings, wherein the element comprises a maze of randomly arranged, interconnected holes for realizing a plurality of random fluid passages through the element, and wherein the element is arranged for performing a flow straightening action at one of an inlet area and an outlet area of the device.

Hence, in the device according to the present invention, at least one flow straightening element is used, which flow straightening element has inlet openings for letting in fluid at one side and outlet openings for letting out fluid at another side, wherein each inlet opening is in communication with a plurality of outlet openings. It may even be so that each inlet opening is in communication with all of the outlet openings. At first sight, it may seem difficult to actually realize such a flow straightening element, and it is a further achievement of the present invention that practical embodiments are proposed. In particular, practical examples of the flow straightening element include an embodiment of the flow straightening element comprising a foam-like material, and an embodiment of the flow straightening element according to which the flow straightening element is shaped like a knitted mesh, for example, a stainless steel knitted mesh. In general, the flow straightening element comprises a maze of randomly arranged, interconnected holes for realizing a plurality of random fluid passages through the element. Furthermore, in general, the flow straightening element may have a clew-like appearance.

As far as the material of the flow straightening element is concerned, it is noted that this may be any suitable type of material, including material having ultraviolet light reflecting properties, and that this may be at least one of a metal material, a ceramic material and a glassy material. Using metal also allows the flow straightening element to be part of an electrical circuit for powering an ultraviolet source such as a lamp. An example of a situation in which this would be advantageous is when an excimer lamp as described in EP 0697374 is used.

Yet another option for the material of the flow straightening element is carbon. For example, the flow straightening element may comprise a compartment of granulated carbon, or a carbon block. Carbon is capable of realizing a diffusing effect in a flow of fluid, while performing a purifying function on the fluid. Furthermore, carbon is capable of removing impurities which may have a negative effect on the ultraviolet source from the fluid. Also, carbon can be used as a filter for removing ozone, which may very well be relevant in the context of applying an ultraviolet source.

The flow straightening element may comprise a copper zinc alloy, which is particularly suitable to be used for purifying water from chlorine. Also, the flow straightening element may be realized as an ion exchanger or a membrane.

According to the invention, an element having inlet openings and outlet openings, wherein each inlet opening is in fluid communication with a plurality of outlet openings, possibly all outlet openings, is used for performing a straightening action on a flow of fluid, so that it is possible to have a controlled flow of fluid through the device comprising the ultraviolet source, i.e. a controlled inflow to and outflow from an irradiated section. In any case, according to the present invention, the flow straightening element does not comprise a plate having a certain pattern of channels, or an assembly of (parallel) baffles, for example, as in such a case, each inlet opening would be in communication with no more than one outlet opening. In this respect, it is noted that an example of a conventional situation in which a baffle wall having a certain pattern of holes is used for laminarizing a flow of water is found in US 2006/0192136. As the flow straightening element according to the present invention has the maze of randomly, arranged interconnected holes, there are no defined channels in the element whatsoever, and the fluid will normally not follow a straight path from an inlet opening to an outlet opening.

On the basis of the presence of a plurality of fluid passages, the flow straightening element of the device according to the present invention has a porous structure, so that pressure losses of fluid flowing through the element are low. Another advantage of an application of the flow straightening element is that an influence of variations in inlet conditions can be minimized. Local high velocities prevailing in a flow of fluid can be dampened. The flow straightening element may be installed upstream and/or downstream of the ultraviolet source, so that the irradiance level of the source does not have to be affected. All in all, a very compact, cost-effective flow straightening element can be realized.

Besides a flow straightening function, the flow straightening element may also have a shielding function. In particular, the flow straightening element may be arranged at a position for shielding at least one area of the device from the ultraviolet light that is emitted by the ultraviolet source during operation of the device. When the flow straightening element is applied for performing a shielding function, there is no contradiction between the shielding function on the one hand, and the function of allowing flow to pass on the other hand, due to porous nature of the element. Consequently, a flow of fluid through the element does hardly experience an influence of the presence of the element, while there is no need for a straight channel leading from one side of the element to the other side which may deteriorate the shielding function of the element.

In a practical embodiment, the device according to the present invention is a device for disinfecting water, which comprises an elongated ultraviolet lamp extending from the water inlet area of the device to the water outlet area of the device, wherein the flow straightening means comprise two flow straightening elements, wherein one of the flow straightening elements is arranged at the water inlet side of the device, and wherein another of the flow straightening elements is arranged at the water outlet side of the device. The ultraviolet lamp may be tube-shaped, and may be any suitable lamp for emitting ultraviolet light, for example, of the type known as UV-C. On the basis of the fact that the flow straightening elements may have a shielding function besides the flow straightening functioning, the positioning of the flow straightening elements determines the positioning of the irradiated section in the device, and the length of this section. Another additional function of the flow straightening elements may be the function of receiving ends of the lamp and supporting the lamp in the device. Furthermore, the lamp may be arranged such as to extend through the flow straightening elements. In that situation, in order to ensure that no ultraviolet light can reach sections of the device outside of the irradiated section, it is preferred to have additional means for covering the utmost ends of the lamp.

Also in case the lamp is not extending through the flow straightening elements, it is advantageous to have means for covering a central portion of another side of the flow straightening element than the side that is facing the irradiated section. The reason for having such means is that in the central area of the flow straightening element, transmission of ultraviolet light is highest, due to light beams entering the flow straightening element at relatively large reflection angles in the central area. Using means for covering the central portion avoid the transmittance of too much ultraviolet light to the area that is shielded from the ultraviolet light by the flow straightening element. Moreover, at the water inlet side, assuming that the device has a central water inlet, the means may have an additional function in reducing the impact of a jet coming from the central inlet and enhancing distribution of the flow of water over the whole inlet surface of the irradiated section. The means as mentioned comprise a metal plate, for example, which has a closed central portion and a number of spokes extending from the central portion. For sake of completeness, it is noted that it is also possible to have means for covering a central portion of the side of the flow straightening element that is facing the irradiated section.

Due to the application of flow straightening elements as shielding elements at both ends of the lamp, it is achieved that other sections than the irradiated sections cannot be reached by the ultraviolet light that is emitted by the lamp during operation. The flow straightening elements block the ultraviolet light, and therefore, it is possible to use any desirable type of seals, bearings and construction materials, which may be less resistant to ultraviolet light, and which may therefore be relatively cheap. Furthermore, the flow straightening elements allow the water to pass, wherein there is a straightening effect on the flow of water, while disturbance of the flow pattern does not occur. Pressure losses are low, while an optimal dose output can be achieved. All in all, the flow straightening elements are capable of providing for optimal shielding and various advantageous influences on the flow of water at the same time. When a flow straightening element is used at the water inlet side, velocity variations at the inlet are very effectively damped out. In order to have a flow of water that is even further optimized, the device according to the present invention may be equipped with means for diverging a flow of fluid, which means are arranged at a position between the water inlet and a flow straightening element arranged at the water inlet side, and/or means for converging a flow of fluid, which means are arranged at a position between the water outlet and a flow straightening element arranged at the water outlet side.

The above-described and other aspects of the present invention will be apparent from and elucidated with reference to the following detailed description of a number of embodiments of a water disinfecting device according to the present invention.

BRIEF DESCRIPTION OF THE DRAWINGS

The present invention will now be explained in greater detail with reference to the figures, in which equal or similar parts are indicated by the same reference signs, and in which.

DETAILED DESCRIPTION OF EMBODIMENTS

Figure 1:
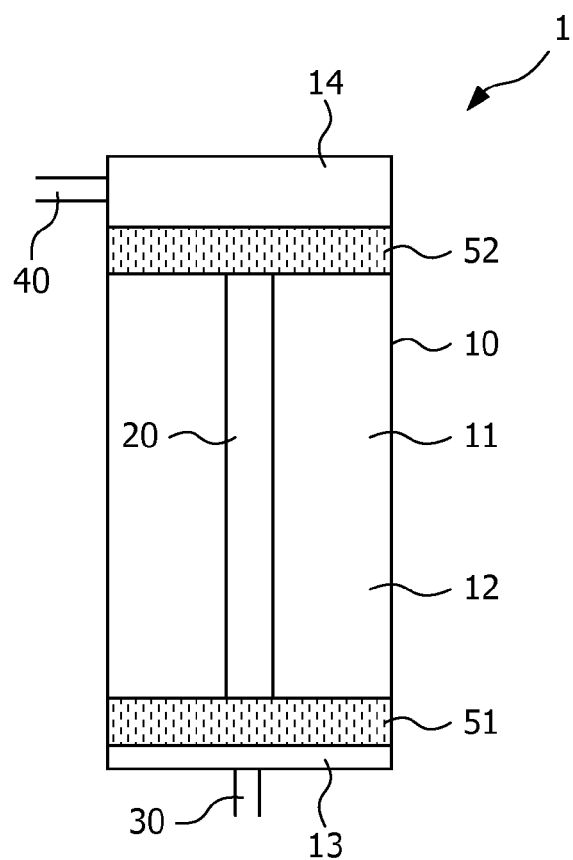
FIG. 1 diagrammatically shows a first embodiment of a water disinfecting device according to the present invention.

FIG. 1 shows a first embodiment 1 of a water disinfecting device according to the present invention. The water disinfecting device 1 comprises the following components: a housing 10; a source 20 for emitting ultraviolet light, which is an ultraviolet lamp 20 in this example, and which is arranged in an interior space 11 of the housing; an inlet 30 for letting in water to be treated by means of ultraviolet radiation to the interior space 11 of the housing 10; an outlet 40 for letting out water from the housing 10; and two flow straightening elements 51, 52, wherein one flow straightening element 51, which will hereinafter be referred to as inlet flow straightening element 51, is arranged at an inlet side of the water disinfecting device 1, i.e. at a position near the inlet 30, and wherein another flow straightening element 52, which will hereinafter be referred to as outlet flow straightening element 52, is arranged at an outlet side of the device 1, i.e. at a position near the outlet 40.

The ultraviolet lamp 20 is arranged in an area of the water disinfecting device 1 which is delimited by the flow straightening elements 51, 52, and which will hereinafter be referred to as irradiated area 12. The inlet flow straightening element 51 has a function in shielding an inlet area 13 of the device 1, i.e. an area where the inlet 30 is located from the influence of the ultraviolet light that is emitted by the ultraviolet lamp 20 during operation, and the outlet flow straightening element 52 has a function in shielding an outlet area 14 of the device 1, i.e. an area where the outlet 40 is located from the influence of the ultraviolet light. In view of the fact that proper operation of the device 1 involves a flow of water from the inlet 30 to the outlet 40, the flow straightening elements 51, 52 are permeable to water. Furthermore, the flow straightening elements 51, 52 are adapted to perform a flow straightening action on a flow of water, as will be explained later. The way in which the water disinfecting device 1 is operated will be explained in the following. Water that is to be subjected to a treatment with ultraviolet light in order to disinfect the water is supplied to the device 1 through the inlet 30. The water flows from the inlet area 13 to the irradiated area 12 through the inlet flow straightening element 51. In the irradiated area 12, the water is exposed to the ultraviolet light that is emitted by the ultraviolet lamp 20, as a result of which microbiological disinfection of the water is achieved. The disinfected water exits the device 1 by passing through the outlet flow straightening element 52 to the outlet area 14, flowing towards the outlet 40, and eventually flowing through the outlet 40.

The present invention relates to the flow straightening elements 51, 52. These elements 51, 52 perform two functions which seem to be contradictory. The main function of the elements 51, 52 is letting pass the water from one side of the element 51, 52 to another side and performing a straightening action on the flow of water in the process. In the second place, there is the function of shielding the inlet area 13 and the outlet area 14 from the ultraviolet radiation. A reason for having a shielding function in the water disinfecting device 1 is the fact that a possibility for using cheap materials in the inlet area 13 and the outlet area 14 is created, in view of the fact that the materials do not need to be resistant to ultraviolet radiation. In the inlet area 13 and the outlet area 14, components such as seals and bearings (now shown in the diagrammatic representation of FIG. 1) are present, and it is advantageous if these components can be components manufactured from polymer materials.

Figure 2:
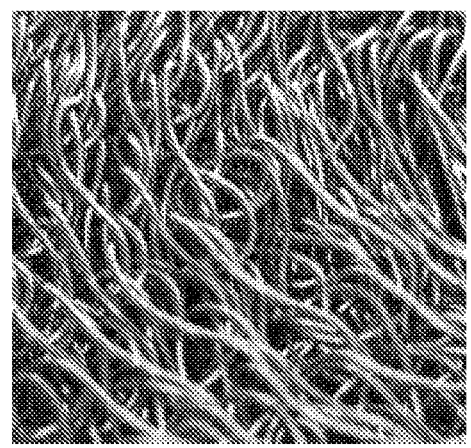
FIG. 2 shows a detail of a flow straightening element that is part of the device shown in FIG. 1.

The flow straightening elements 51, 52 of the device 1 according to the present invention are different from comparable elements known in the art. In particular, the flow straightening elements 51, 52 are not realized as plates having one or more holes for allowing the water to pass. Instead, each inlet opening of the flow straightening elements 51, 52 is in fluid communication with a plurality of outlet openings, so that a structure in which a plurality of fluid passages extends from each inlet opening is realized. For example, the flow straightening elements 51, 52 may have a clew-like appearance, and may comprise a foam-like material or may have a meshy structure. In FIG. 2, an example of a structure of a flow straightening element 51, 52 is shown, wherein the flow straightening element 51, 52 comprises a knitted mesh. The material of the flow straightening element 51, 52 may be stainless steel, for example. In any case, the flow straightening element 51, 52 does not need to be an expensive element, while it is still possible to achieve excellent flow straightening results.

Figure 3:
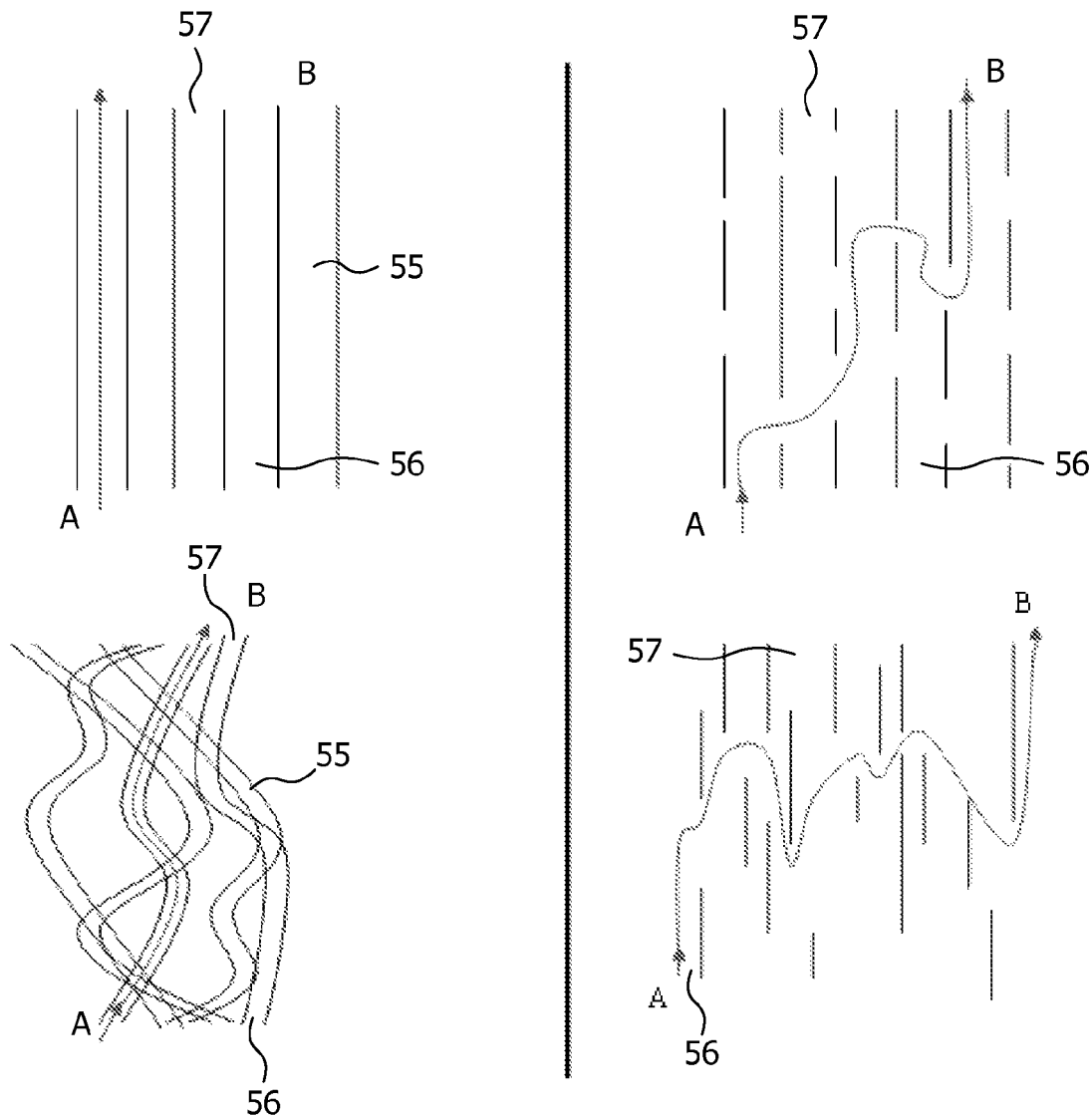
FIG. 3 illustrates differences between a flow pattern in a conventional flow straightening structure having channels with continuous walls and a flow pattern in a structure according to the present invention.

FIG. 3 illustrates the differences between a flow pattern in a conventional flow straightening structure having channels with continuous walls and a flow pattern in a structure according to the present invention. On the left side of the figure, the conventional situation is illustrated on the basis of two examples. In a first example, a plurality of straight channels 55 having continuous, closed walls is applied. A flow of water through one of the channels 55 is illustrated by means of an arrow. It is clear that the path of the water from one side (A) of the structure to another side (B) of the structure is defined by the continuous, closed walls. Hence, in the conventional situation, the flow path is from one inlet opening 56 to one outlet opening 57. This fact is also found in another example, wherein a plurality of curved channels 55 having continuous, closed walls is applied. In this case, although the channels 55 are curved, it is also possible to exactly predict at which outlet opening 57 a water element will exit the structure once the inlet opening 56 at which the water element enters the structure is known.

On the right side of FIG. 3, the situation according to the present invention is illustrated. In the structure according to the present invention, it is not possible to discern channels having continuous walls that are extending along an entire length of the structure, from one inlet opening 56 to one outlet opening 57. Instead, the structure is a kind of maze, wherein all inlet openings 56 are in communication with all outlet openings 57. In such a structure, a water element that is moving from one side (A) of the structure to another side (B) may take one of various paths, depending on the way (velocity, direction) in which the water element enters an inlet opening 56. FIG. 3 shows two different flow paths through a structure according to the present invention, wherein the flow paths are indicated as an arrow. A major advantage of the structure according to the present invention is that variations in inlet conditions can be dampened. Hence, the structure according to the present invention is porous on the one hand, so that a pressure drop over the structure can be minimal, and has an excellent flow straightening performance on the other hand.

Figure 4:
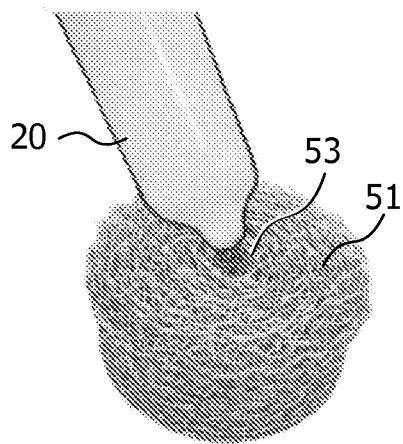
FIGS. 4 and 5 illustrate how a flow straightening element can be used for supporting a lamp in the device.
Figure 5:
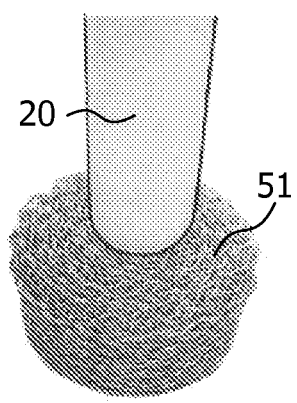

The length in the direction of the flow and the porosity of the flow straightening element 51, 52 can be chosen such that the flow straightening function and the shielding function are maximized, whereas pressure losses in the flow of water are minimized. Furthermore, it is possible to apply the flow straightening element 51, 52 as a support of the ultraviolet lamp 20, wherein there is no need for additional support elements, or wherein at least less additional support elements are required. This possibility is illustrated by means of FIGS. 4 and 5, in which it is shown how the flow straightening element 51, 52 can be provided with a central cavity 53, and how an end of the ultraviolet lamp 20 can be inserted in this cavity 53.

Figure 6:
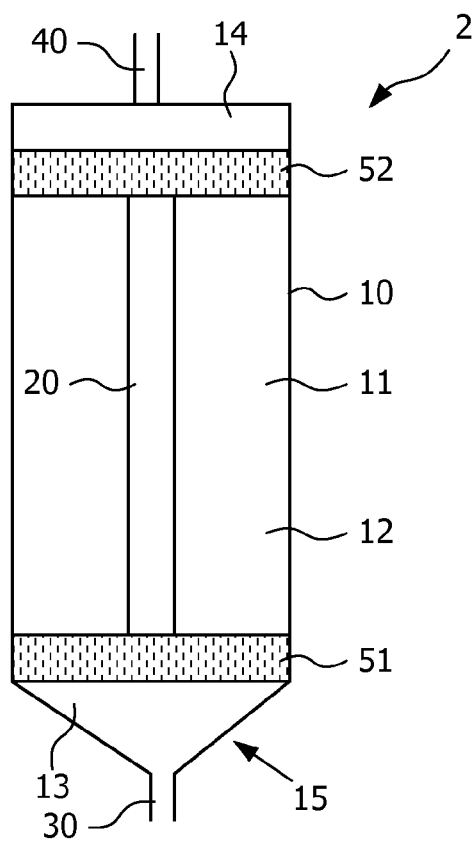
FIG. 6 diagrammatically shows a second embodiment of a water disinfecting device according to the present invention.

FIG. 6 shows a second embodiment 2 of a water disinfecting device according to the present invention. The water disinfecting device 2 according to the second embodiment of the present invention resembles the water disinfecting device 1 according to the first embodiment to a large extent. Yet, there is a difference, which resides in the fact that the water disinfecting device 2 according to the second embodiment comprises a flow diffuser 15 in the inlet area 13, whereas the water disinfecting device 1 according to the first embodiment does not. The optional flow diffuser 15 is positioned upstream of the inlet flow straightening element 51, and has a function in expanding the flow of water in a controlled manner to the inlet flow straightening element 51. It is also possible that means (not shown) for contracting the flow in a controlled manner towards the outlet 40 of the water disinfecting device 1, 2 are provided and arranged in the outlet area 14, i.e. downstream of the outlet flow straightening element 52. Using the flow diffuser 15 and/or such means contribute to smoothness of a flow of water through the water disinfecting device 1, 2, which contributes to the effectiveness of the ultraviolet light treatment.

Figure 7:
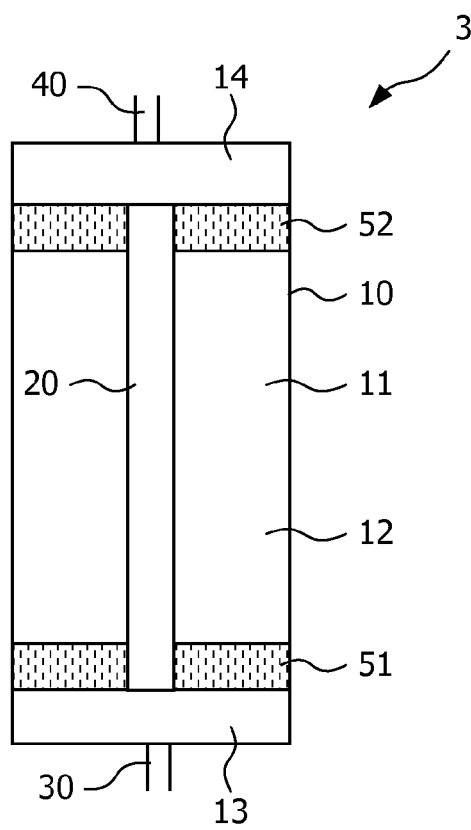
FIG. 7 diagrammatically shows a third embodiment of a water disinfecting device according to the present invention.

FIG. 7 shows a third embodiment 3 of a water disinfecting device according to the present invention. In this embodiment, ends of the ultraviolet lamp 20 are extending all the way through the flow straightening elements 51, 52. In other words, the flow straightening elements 51, 52 are surrounding the ends of the ultraviolet lamp 20. An advantage of this configuration is that the supporting function of the flow straightening elements 51, 52 for the ultraviolet lamp 20 is optimal, wherein it is surely not necessary to use other support elements.

Ultraviolet light that enters fluid passages of the flow straightening element 51, 52 at a position near the outer circumference of the flow straightening element 51, 52 has traveled a relatively long distance through the water, when the ultraviolet lamp 20 has a central positioning with respect to the flow straightening element 51, 52, as is the case in the shown examples. Drinking water has an ultraviolet transmission coefficient of about 0.99 per mm, i.e. 1% of the ultraviolet output is absorbed after 1 mm. Thus, light that has traveled 50 mm, for example, from the ultraviolet lamp 20 to the outer fluid passages of a flow straightening element 51, 52, has lost about 40% irradiance. Due to internal reflections in the flow straightening element 51, 52, the irradiance level is reduced further. In this respect, it is noted that metal surfaces may reflect incident ultraviolet light up to about 60%. Light that is irradiated closer to the flow straightening element 51, 52, does not loose much irradiance due to absorption by the water. However, as the reflection angle of such light beams is smaller, considerable loss of irradiance occurs anyway, due to reflection. This means that despite the fact that some light beams enter the outer fluid passages of the flow straightening element 51, 52 with relatively high ultraviolet power, reflection ensures that this power is reduced on short distances.

Figure 8:
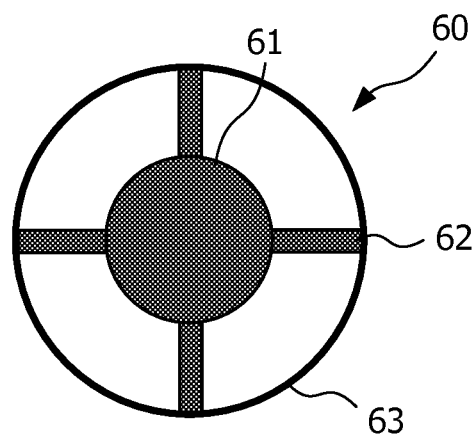
FIG. 8 diagrammatically shows a flow plate that can be used in the device shown in FIG. 7.
Figure 9:
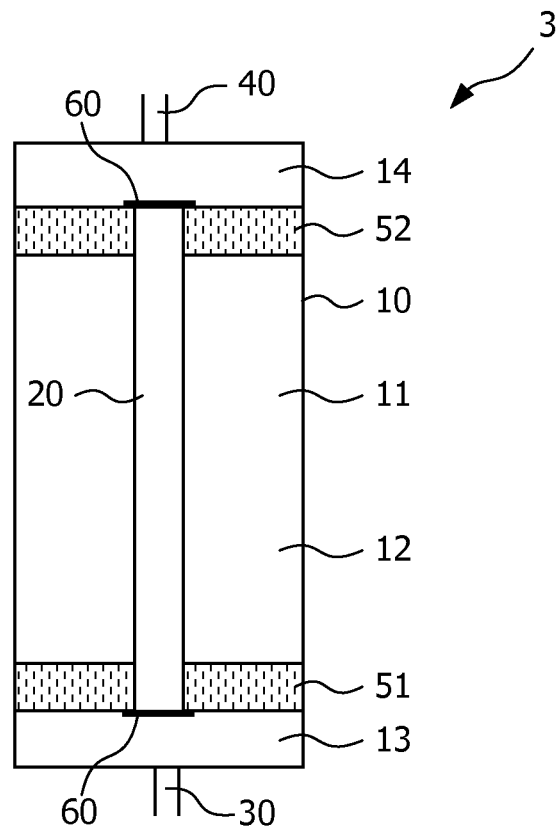
FIG. 9 illustrates the positioning of two flow plates in the device shown in FIG. 7.

Transmission of ultraviolet light increases from the fluid passages at the outer circumference of the flow straightening element 51, 52 to the fluid passages closer to a central axis of the flow straightening element 51, 52. The transmission is highest for light entering the fluid passages in a central area of the flow straightening element 51, 52. A portion of the transmitted light through the central area of the flow straightening element 51, 52 is due to light beams arriving at large reflection angles. As both absorption and reflection levels of such light beams are low, not much ultraviolet power is lost. The irradiance level in the central area can be reduced by placing a plate, for example a metal plate, which is closed in a central area, upstream and downstream of respectively the inlet flow straightening element 51 and the outlet flow straightening element 52. An example of such a plate 60 is shown in FIG. 8. Besides a closed central portion 61, the plate 60 comprises spokes 62 extending from the central portion 61, so that the plate 60 does hardly hinder a flow of water outside of the central area of the flow straightening element 51, 52 at which it is arranged. In the shown example, the plate 60 furthermore comprises an outer ring 63. The positioning of the plates 60 in a water purifying device 3 according to the present invention is illustrated in FIG. 9. At the inlet side, the application of the plate 60 offers an additional advantage, as the plate 60 has a function in reducing the impact of the jet coming from the inlet 30 and enhancing distribution of the flow of water over the entire inlet surface of the irradiated area 12.

For sake of completeness, it is noted that the plate 60 as shown is just one example of the many possibilities for means which are suitable for blocking ultraviolet radiation in less effective areas of the flow straightening elements 51, 52, and which are designed such as to not disturb a flow pattern of the water.

In respect of the flow straightening element 51, 52 as described in the foregoing, it is noted that both the pressure loss of a flow of water over the flow straightening element 51, 52 and penetration of ultraviolet light through the flow straightening element 51, 52 can be minimized. Two relevant properties of the flow straightening element 51, 52 in this context are a length of the flow straightening element 51, 52 and a pore size of the material of the flow straightening element 51, 52. For the pore size as mentioned, the following design rule may be applied:

$$\frac{t}{d} \geq 0.03 Re$$

wherein t is the thickness of the flow straightening element 51, 52; d is the pore size of the material of the flow straightening element 51, 52; and Re is the Reynolds number in pores, which is given by the following relation:

$$Re = \frac{v(D_o - D_i)}{\upsilon} = \frac{4Q}{\pi \upsilon (D_o + D_i)}$$

wherein v is the fluid velocity; $D_o$ is the outer diameter of the flow straightening element 51, 52, or the diameter of the irradiated section 12; $D_i$ is the inner diameter of the flow straightening element 51, 52, or the diameter of the ultraviolet lamp 20; $\upsilon$ is the kinematic viscosity; and Q is the fluid flow rate.

In order to minimize penetration of the ultraviolet light, t/d is preferably as large as possible, whereas for pressure loss minimization, t/d should be as small possible. In view of this, the following is applicable in practical situations:

$$1 \leq \frac{t}{d} \leq 500, \text{ preferably } 1 \leq \frac{t}{d} \leq 150, \text{ preferably } 5 \leq \frac{t}{d} \leq 50$$

Instead of the pore size, the porosity p of the material of the flow straightening element 51, 52 can be chosen as a design parameter. For example, a porosity p of 0.9 means that 90% of the structure is open. The following ranges may now be taken into account:

$$5 \leq \frac{t}{p} \leq 500, \text{ preferably } 25 \leq \frac{t}{p} \leq 250$$

wherein t has a dimension of mm.

Another important design parameter for the ultraviolet light blocking property of the material of the flow straightening element 51, 52 is the ratio of the length of the lamp 20 versus the outer diameter of the flow straightening element 51, 52, $L/D_o$, wherein L is the length of the lamp 20 and $D_o$ is the outer diameter of the flow straightening element 51, 52. The following range of this ratio is applicable:

$$0.5 \leq \frac{L}{D_o} \leq 10, \text{ preferably } 0.5 \leq \frac{L}{D_o} \leq 5$$

It is noted that tests have proven that it is possible to achieve a situation in which ultraviolet light is totally blocked by a flow straightening element 51, 52 that is provided in the form of a stainless steel knitted mesh. During the tests, stainless steel knitted meshes were used from KnitMesh Ltd, Greenfield, Great Britain. The knitted meshes had a diameter of 42 mm and a thickness of 20 mm. It was found that with a knitted mesh that has an openness of 85% or less, it is sure that ultraviolet light is totally blocked.

It will be clear to a person skilled in the art that the scope of the present invention is not limited to the examples discussed in the foregoing, but that several amendments and modifications thereof are possible without deviating from the scope of the present invention as defined in the attached claims. While the present invention has been illustrated and described in detail in the figures and the description, such illustration and description are to be considered illustrative or exemplary only, and not restrictive. The present invention is not limited to the disclosed embodiments.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope of the present invention.

In general, the present invention is applicable in devices in which a source for generating/emitting ultraviolet light is arranged, and in which there is a flow of fluid during operation of the device, wherein it is important to control the flow of fluid by means for straightening the flow. For sake of completeness, it is noted that the fact that water is mentioned as an example of a fluid should not be understood such as to mean that the present invention is limited to that type of fluid. Furthermore, it is noted that in the context of this description, the terms "ultraviolet light" and "ultraviolet radiation" are used to indicate one and the same phenomenon, namely waves having a wave length in the ultraviolet region.

The flow straightening means of the device 1, 2, 3 according to the present invention do not necessarily need to comprise two elements 51, 52. It is also possible that only one flow straightening element 51, 52 is used in the device 1, 2, 3, or more than two, depending on the requirements of a specific case. It is preferred if at least one flow straightening element 51, 52 is arranged at a side of the device 1, 2, 3 where an inlet of the fluid is present.

It is also possible for the flow straightening element 51, 52 to be solely used for the purpose of protecting certain areas 13, 14 against the influence of ultraviolet light, i.e. to only have a shielding function and to serve as a shielding element, wherein the device in which the shielding element 51, 52 is arranged does not need to be a device 1, 2, 3 that is intended to accommodate a flow of fluid. In any case, the device can be defined as follows: device, comprising a source 20 for emitting ultraviolet light, and means 51, 52 for shielding at least one area of the device from the ultraviolet light that is emitted by the source 20 during operation of the device, wherein the shielding means comprise at least one element 51, 52 having openings 56, 57 at different sides (A, B), wherein each opening 56 at one side (A) is in communication with a plurality of openings 57 at another side (B).

The present invention can be summarized as follows. A device 1, 2, 3 comprises a source 20 for emitting ultraviolet light, an inlet 30 for letting in fluid to the device 1, 2, 3, an outlet 40 for letting out fluid from the device 1, 2, 3, and means 51, 52 for performing a straightening action on a flow of fluid through the device 1, 2, 3. In feasible practical situations, the device 1, 2, 3 is a device for treating a fluid by exposing the fluid to ultraviolet light, for example, a device 1, 2, 3 for disinfecting water.

The flow straightening means comprise at least one flow straightening element 51, 52 having inlet openings 56 for letting in fluid at one side (A) and outlet openings 57 for letting out fluid at another side (B), wherein each inlet opening 56 is in communication with a plurality of outlet openings 57, and wherein the element 51, 52 comprises a maze of randomly arranged, interconnected holes for realizing a plurality of random fluid passages through the element 51, 52. In such a structure, a water element that is moving from one side (A) of the flow straightening element 51, 52 to another side (B) may take one of various paths, as a result of which variations in inlet conditions can be dampened. Moreover, the flow straightening element 51, 52 is arranged for performing a flow straightening action at one of an inlet area 13 and an outlet area 14 of the device 1, 2, 3, and may have an additional function in blocking ultraviolet light.

The flow straightening effect of the flow straightening element 51, 52 on the flow of fluid contributes to the effectiveness of the treatment of the fluid. In a practical embodiment, the flow straightening element 51, 52 comprises a stainless steel knitted mesh, which is easy to manufacture and relatively cheap.

The invention claimed is:

1. A device, comprising:
  a source for emitting ultraviolet light, an inlet for letting in fluid to the device,
  an outlet for letting out fluid from the device, and
  means for performing a straightening action on a flow of fluid through the device,
  wherein the flow straightening means are arranged in a fluid path from the inlet to the outlet, and
  wherein the flow straightening means comprise an inlet flow straightening element arranged at an inlet area of the device having a first plurality of inlet openings for letting in fluid at one side (A) and a first plurality of outlet openings for letting out fluid at another side (B),
  an outlet flow straightening element arranged at an outlet area of the device having a second plurality of inlet openings for letting in fluid at one side (A) and a second plurality of outlet openings for letting out fluid at another side(B),
  wherein said first plurality of inlet openings is in fluid communication with said plurality of said first outlet openings,
  wherein said second plurality of inlet openings is in fluid communication with said second plurality of outlet openings,
  wherein the inlet flow straightening element and the outlet flow straightening element each comprise a maze of randomly arranged, interconnected holes for realizing a plurality of randomly arranged fluid passages through the respective elements,
  wherein the element is arranged for performing a flow straightening action at one of an inlet area and an outlet area of the device, and
  wherein the inlet flow straightening element is arranged at a position for shielding at least one area of the device from the ultraviolet light that is emitted by the ultraviolet source during operation of the device, and
  wherein the outlet flow straightening element is arranged at a position for shielding at least one other area of the device from the ultraviolet light that is emitted by the ultraviolet source during operation of the device.

2. The device according to claim 1, wherein each inlet opening of the flow straightening element is in communication with all of the outlet openings.

3. The device according to claim 1, wherein the flow straightening element comprises a foam-like material.

4. The device according to claim 1, wherein the flow straightening element is shaped as a knitted mesh.

5. The device according to claim 1, wherein means (60) are provided for covering a central portion of another side of the flow straightening element than the side that is facing an area of the device where the ultraviolet source is arranged.

6. The device according to claim 1, wherein the flow straightening element comprises material having ultraviolet light reflecting properties.

7. The device, according to claim 1, wherein the flow straightening element comprises at least one of a metal material, a ceramic material and a glassy material.

8. The device according to claim 1, wherein the flow straightening element comprises carbon.

9. The device according to claim 1, wherein the ultraviolet source comprises an elongated ultraviolet lamp, wherein the flow straightening element is adapted to receive an end of the lamp and to support the lamp in the device.

10. The device according to claim 9, wherein the lamp is extending through the flow straightening element, and means are provided for covering an utmost end of the lamp.

11. The device according to claim 1, further comprising at least one of means for diverging a flow of fluid, which means are arranged in the inlet area of the device, and means for converging a flow of fluid, which means are arranged in the outlet area of the device.

12. The device according to claim 1, wherein a ratio of a thickness (t) of the flow straightening element and a pore size (d) of the material of the flow straightening element is in a range of 1 to 500.

13. The device according to claim 1, wherein a ratio of a thickness (t) of the flow straightening element and porosity (p) of the material of the flow straightening element is in a range of 5 mm to 500 mm.

14. The device according to claim 1, wherein a ratio of a length (L) of the ultraviolet source (20) and an outer diameter ($D_o$) of the flow straightening element is in a range of 0.5 to 10.

* * * * *